(12) United States Patent
Poon et al.

(10) Patent No.: US 10,434,329 B2
(45) Date of Patent: Oct. 8, 2019

(54) AUTOFOCUS WIRELESS POWER TRANSFER TO IMPLANTABLE DEVICES IN FREELY MOVING ANIMALS

(71) Applicant: THE BOARD OF TRUSTEES OF THE LELAND STANFORD JUNIOR UNIVERSITY, Stanford, CA (US)

(72) Inventors: Ada Shuk Yan Poon, Redwood City, CA (US); John S. Y. Ho, Stanford, CA (US); Yuji Tanabe, Stanford, CA (US); Alexander J. Yeh, Palo Alto, CA (US); Kate L. Montgomery, Palo Alto, CA (US); Logan Grosenick, Palo Alto, CA (US); Emily A. Ferenczi, Palo Alto, CA (US); Vivien Tsao, Stanford, CA (US); Shrivats Mohan Iyer, Palo Alto, CA (US); Scott Lee Delp, Stanford, CA (US); Karl Deisseroth, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 15/306,495

(22) PCT Filed: Mar. 25, 2015

(86) PCT No.: PCT/US2015/022509
§ 371 (c)(1),
(2) Date: Oct. 25, 2016

(87) PCT Pub. No.: WO2015/171213
PCT Pub. Date: Nov. 12, 2015

(65) Prior Publication Data
US 2017/0065828 A1    Mar. 9, 2017

Related U.S. Application Data

(60) Provisional application No. 61/991,266, filed on May 9, 2014.

(51) Int. Cl.
*A61N 5/06* (2006.01)
*A61N 1/36* (2006.01)
(Continued)

(52) U.S. Cl.
CPC .......... *A61N 5/0622* (2013.01); *A61B 5/0031* (2013.01); *A61N 1/0529* (2013.01);
(Continued)

(58) Field of Classification Search
None
See application file for complete search history.

(56) References Cited

U.S. PATENT DOCUMENTS 3,902,501 A  9/1975 Citron et al.
3,939,843 A  2/1976 Smyth
(Continued)

FOREIGN PATENT DOCUMENTS

WO  WO2009/008932 A2  1/2009
WO  WO2011/150430 A2  12/2011
(Continued)

OTHER PUBLICATIONS

Zhao et al., RF evanescent-mode cavity resonator for passive wireless sensor applications, Sensors and Actuators A 161 (2010) 322-328.*
(Continued)

*Primary Examiner* — Carl H Layno
*Assistant Examiner* — Manolis Pahakis
(74) *Attorney, Agent, or Firm* — Shay Glenn LLP

(57) ABSTRACT

A power transmitter is provided that can include a microwave cavity resonant at a desired operating frequency, a
(Continued)

hexagonal mesh top to leak evanescent fields out of the cavity, and a plurality of orthogonal monopole feeds with 90 degrees phase differences creating circularly polarized waves. The power transmitter can be configured to transmit energy to a wireless device implanted in an animal passing through the evanescent fields. Implantable devices are also described which can receive wireless energy from the power transmitter and stimulate the animals (e.g., optogenetic or electrical stimulation).

9 Claims, 13 Drawing Sheets

(51) Int. Cl.
  *A61B 5/00* (2006.01)
  *A61N 1/378* (2006.01)
  *A61N 1/05* (2006.01)
  *A61N 1/372* (2006.01)

(52) U.S. Cl.
  CPC ......... *A61N 1/3605* (2013.01); *A61N 1/3787* (2013.01); *A61N 5/0601* (2013.01); *A61B 2503/40* (2013.01); *A61B 2560/0219* (2013.01); *A61N 1/37205* (2013.01)

(56) References Cited

U.S. PATENT DOCUMENTS

| | | |
|---|---|---|
| 4,033,357 A | 7/1977 | Helland et al. |
| 4,236,529 A | 12/1980 | Little |
| 4,262,678 A | 4/1981 | Stokes |
| 4,269,198 A | 5/1981 | Stokes |
| 4,301,815 A | 11/1981 | Doring |
| 4,407,303 A | 10/1983 | Akerstrom |
| 4,409,994 A | 10/1983 | Doring |
| 4,506,679 A | 3/1985 | Mann |
| 4,582,069 A | 4/1986 | McArthur |
| 4,592,356 A | 6/1986 | Gutierrez |
| 4,658,835 A | 4/1987 | Pohndorf |
| 4,716,888 A | 1/1988 | Wesner |
| 4,721,118 A | 1/1988 | Harris |
| 4,796,643 A | 1/1989 | Nakazawa et al. |
| 4,841,971 A | 6/1989 | Hess |
| 4,883,070 A | 11/1989 | Hanson |
| 4,945,922 A | 8/1990 | van Krieken |
| 4,957,118 A | 9/1990 | Erlebacher |
| 5,193,539 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,358,514 A | 10/1994 | Schulman et al. |
| 5,545,206 A | 8/1996 | Carson |
| 5,662,697 A | 9/1997 | Li et al. |
| 5,814,089 A | 9/1998 | Stokes et al. |
| 5,833,603 A | 11/1998 | Kovacs et al. |
| 5,868,741 A | 2/1999 | Chia et al. |
| 5,908,433 A | 6/1999 | Eager et al. |
| 5,953,223 A | 9/1999 | Kato et al. |
| 5,957,965 A | 9/1999 | Moumane et al. |
| 6,021,354 A | 2/2000 | Warman et al. |
| 6,141,588 A | 10/2000 | Cox et al. |
| 6,164,284 A | 12/2000 | Schulman et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,304,613 B1 | 10/2001 | Koller et al. |
| 6,304,786 B1 | 10/2001 | Heil et al. |
| 6,324,434 B2 | 11/2001 | Coe et al. |
| 6,405,091 B1 | 6/2002 | Vachon et al. |
| 6,482,152 B2 | 11/2002 | Kim |
| 6,510,347 B2 | 1/2003 | Borkan |
| 6,659,352 B1 | 12/2003 | Asada et al. |
| 6,678,179 B2 | 1/2004 | Buehring |
| 7,191,007 B2 * | 3/2007 | Desai ................... A61N 1/3787 607/33 |
| 7,191,013 B1 | 3/2007 | Miranda et al. |
| 7,289,028 B2 | 10/2007 | Kofler |
| 7,573,368 B2 | 3/2009 | Conraux |
| 7,703,677 B2 | 4/2010 | Allhodzic |
| 7,756,223 B2 | 7/2010 | Missoni |
| 8,120,487 B2 | 2/2012 | Chang et al. |
| 8,280,272 B2 | 10/2012 | Kim |
| 8,299,652 B2 * | 10/2012 | Sample ................... H02J 5/005 307/104 |
| 8,452,421 B2 | 5/2013 | Thenuwara et al. |
| 8,497,658 B2 | 7/2013 | Von Novak et al. |
| 8,538,541 B2 | 9/2013 | Milojevic et al. |
| 8,634,928 B1 | 1/2014 | O'Driscoll et al. |
| 8,641,644 B2 * | 2/2014 | Freeman ............. A61B 5/14532 600/584 |
| 8,655,451 B2 | 2/2014 | Klosterman et al. |
| 8,855,786 B2 * | 10/2014 | Derbas ................. A61N 1/0553 607/68 |
| 8,891,270 B2 | 11/2014 | Song et al. |
| 8,901,775 B2 | 12/2014 | Armstrong et al. |
| 8,901,778 B2 * | 12/2014 | Kesler ...................... H03H 7/40 307/104 |
| 8,901,779 B2 * | 12/2014 | Kesler ...................... H03H 7/40 307/104 |
| 8,937,825 B2 | 1/2015 | Lee |
| 8,972,502 B2 | 3/2015 | Beslic et al. |
| 9,276,457 B2 | 3/2016 | Taillardat |
| 9,367,734 B2 | 6/2016 | Tramoni |
| 9,504,842 B2 | 11/2016 | Guardiani et al. |
| 9,537,428 B2 | 1/2017 | Hytten et al. |
| 9,592,397 B2 | 3/2017 | Hansen et al. |
| 9,692,324 B2 | 6/2017 | Bleier et al. |
| 9,821,159 B2 * | 11/2017 | Ackermann ....... A61N 1/36046 |
| 9,831,681 B2 | 11/2017 | Shimokawa |
| 9,831,719 B2 | 11/2017 | Lee et al. |
| 10,004,913 B2 * | 6/2018 | Poon ...................... H02J 5/005 |
| 2001/0044588 A1 | 11/2001 | Mault |
| 2001/0051766 A1 * | 12/2001 | Gazdzinski ........ A61B 1/00016 600/309 |
| 2002/0042637 A1 | 4/2002 | Stover |
| 2003/0055406 A1 | 3/2003 | Lebel et al. |
| 2003/0158584 A1 | 8/2003 | Cates et al. |
| 2004/0193229 A1 | 9/2004 | Starkebaum et al. |
| 2005/0043765 A1 | 2/2005 | Williams et al. |
| 2005/0151696 A1 | 7/2005 | Govari et al. |
| 2005/0245989 A1 | 11/2005 | Davis |
| 2005/0288596 A1 | 12/2005 | Eigler et al. |
| 2006/0061323 A1 * | 3/2006 | Cheng ..................... H02J 5/005 320/108 |
| 2006/0074450 A1 | 4/2006 | Boveja et al. |
| 2006/0149330 A1 | 7/2006 | Mann et al. |
| 2006/0161225 A1 | 7/2006 | Sormann et al. |
| 2006/0210279 A1 * | 9/2006 | Hillis ..................... B82Y 20/00 398/118 |
| 2006/0224225 A1 | 10/2006 | Ransbury et al. |
| 2006/0241524 A1 * | 10/2006 | Lee ................... A61B 17/22012 601/2 |
| 2006/0253044 A1 | 11/2006 | Zhang et al. |
| 2007/0032734 A1 | 2/2007 | Najafi et al. |
| 2007/0156205 A1 | 7/2007 | Larson et al. |
| 2007/0222542 A1 * | 9/2007 | Joannopoulos ....... B60L 11/182 333/219 |
| 2007/0282378 A1 | 12/2007 | Huang et al. |
| 2008/0021532 A1 | 1/2008 | Kveen et al. |
| 2008/0039904 A1 | 2/2008 | Bulkes et al. |
| 2008/0045989 A1 | 2/2008 | Welborn |
| 2008/0103578 A1 | 5/2008 | Gerber |
| 2008/0132981 A1 | 6/2008 | Gerber |
| 2008/0161803 A1 | 7/2008 | Oral et al. |
| 2008/0197710 A1 * | 8/2008 | Kreitz ................... B25J 19/0029 307/104 |
| 2008/0300654 A1 | 12/2008 | Lambert et al. |
| 2008/0300660 A1 | 12/2008 | John |
| 2009/0105782 A1 | 4/2009 | Mickle et al. |
| 2009/0128262 A1 * | 5/2009 | Lee .......................... H01Q 7/00 333/219.1 |

(56) References Cited

U.S. PATENT DOCUMENTS

| | | |
|---|---|---|
| 2009/0157147 A1 | 6/2009 | Cauller et al. |
| 2009/0171408 A1 | 7/2009 | Solem |
| 2009/0187230 A1 | 7/2009 | Dilorenzo |
| 2009/0204170 A1 | 8/2009 | Hastings et al. |
| 2009/0275956 A1 | 11/2009 | Burnes et al. |
| 2009/0281597 A1 | 11/2009 | Parramon et al. |
| 2009/0292336 A1 | 11/2009 | Nishida et al. |
| 2010/0081895 A1 | 4/2010 | Zand |
| 2010/0145418 A1* | 6/2010 | Zhang ............... A61N 5/06 607/92 |
| 2010/0161002 A1 | 6/2010 | Aghassian et al. |
| 2010/0168817 A1 | 7/2010 | Yamamoto et al. |
| 2010/0264748 A1* | 10/2010 | Tucker ............... H01Q 7/00 307/104 |
| 2010/0292629 A1 | 11/2010 | Dacey et al. |
| 2011/0034886 A1 | 2/2011 | Elbe et al. |
| 2011/0093036 A1 | 4/2011 | Mashiach |
| 2011/0125078 A1* | 5/2011 | Denison ............... A61N 5/0601 604/20 |
| 2011/0144510 A1 | 6/2011 | Ryu et al. |
| 2011/0184337 A1 | 7/2011 | Evans et al. |
| 2011/0190849 A1 | 8/2011 | Faltys et al. |
| 2011/0276110 A1 | 11/2011 | Whitehurst et al. |
| 2011/0301670 A1 | 12/2011 | Gross et al. |
| 2012/0004708 A1 | 1/2012 | Chen et al. |
| 2012/0123508 A1* | 5/2012 | Wentz ............... A61N 1/3787 607/88 |
| 2012/0197352 A1 | 8/2012 | Carbunaru et al. |
| 2012/0203306 A1 | 8/2012 | Sarvazyan |
| 2012/0235500 A1* | 9/2012 | Ganem ............... H03H 7/40 307/104 |
| 2012/0235634 A1* | 9/2012 | Hall ............... H03H 7/40 320/108 |
| 2012/0245444 A1 | 9/2012 | Otis et al. |
| 2012/0253261 A1* | 10/2012 | Poletto ............... A61M 5/14276 604/20 |
| 2012/0283800 A1 | 11/2012 | Perryman et al. |
| 2012/0296329 A1 | 11/2012 | Ng |
| 2012/0330384 A1 | 12/2012 | Perryman et al. |
| 2013/0012866 A1 | 1/2013 | Deem et al. |
| 2013/0023943 A1 | 1/2013 | Parramon et al. |
| 2013/0053767 A1 | 2/2013 | Pivonka et al. |
| 2013/0079861 A1 | 3/2013 | Reinert et al. |
| 2013/0141794 A1 | 6/2013 | Najiminaini et al. |
| 2013/0211469 A1 | 8/2013 | Lamont et al. |
| 2013/0215979 A1 | 8/2013 | Yakovlev et al. |
| 2013/0261703 A1 | 10/2013 | Chow et al. |
| 2013/0310901 A1 | 11/2013 | Perryman et al. |
| 2013/0336095 A1* | 12/2013 | Seppa ............... G01L 9/0016 367/137 |
| 2014/0142507 A1 | 5/2014 | Armes |
| 2014/0203823 A1 | 7/2014 | Joshi |
| 2014/0275847 A1 | 9/2014 | Perryman et al. |
| 2014/0288393 A1 | 9/2014 | Grevious et al. |
| 2014/0324138 A1* | 10/2014 | Wentz ............... A61N 5/0622 607/92 |
| 2015/0249344 A1 | 9/2015 | Poon et al. |
| 2015/0335285 A1 | 11/2015 | Poon et al. |
| 2016/0113671 A1 | 4/2016 | Berger |
| 2016/0228183 A1* | 8/2016 | Urzhumov ............ A61B 18/18 |
| 2016/0228720 A1* | 8/2016 | Urzhumov ............ A61N 1/406 |
| 2017/0095667 A1 | 4/2017 | Yakovlev et al. |
| 2018/0296849 A1 | 10/2018 | Poon et al. |

FOREIGN PATENT DOCUMENTS

| | | |
|---|---|---|
| WO | WO2013/035092 A2 | 3/2013 |
| WO | WO2014/006510 A2 | 1/2014 |
| WO | WO2014/153219 A1 | 9/2014 |
| WO | WO2014/153228 A1 | 9/2014 |
| WO | WO2015/039108 A2 | 3/2015 |
| WO | WO2015/196164 A2 | 12/2015 |
| WO | WO2016/127130 A1 | 8/2016 |

OTHER PUBLICATIONS

Poher et al., Micro-LED arrays: a tool for two-dimensional neuron stimulation, J. Phys. D: Appl. Phys. 41 (2008).*
Liou et al., Wireless Charging System of Mobile Handset Using Metamaterial Based Cavity Resonator, IEEE, 2012.*
Wentz et al., A Wirelessly Powered and Controlled Device for Optical Neural Control of Freely-Behaving Animals, J Neural Eng. Aug. 2011 ; 8(4).*
Ball; Wireless power for tiny medical devices; Physics; 6; 57; 3 pages; May 17, 2013.
Ho et al.; Midfield wireless powering for implantable systems; Proc. IEEE; vol. 101; No. 6; Apr. 4, 2013; 10 pages; retrieved Apr. 21, 2014 from the internet: http://web.stanford.edu/group/poongroup/cgi-bin/wordpress/wp-content/uploads/2013/05/PIEEE%202013%20Ho.pdf.
Kim et al.; Midfield wireless powering of subwavelength autonomous devices; Phys. Rev. Lett.; 110(20); 203905; May 17, 2013.
Kim et al.; Wireless power transfer to a cardiac implant; Appl. Phys. Lett.; 101; 073701; 2012; 5 pages; Aug. 13, 2012.
Kim et al.; Wireless power transfer to miniature implants: transmitter optimization; IEEE Trans. Antennas and Propagation; vol. 60; No. 10; pp. 4838-4845; Oct. 2012.
Park et al.; Enhancement of wireless power transmission into biological tissues using a high surface impedance ground plane; Progress in Electromagnetics Research; 135; pp. 123-136; 2013; retrieved Apr. 29, 2015 from the internet: http://onlinewww.jpier.org/PIER/pier135/08.12110902.pdf.
Thomas et al.; Modulated backscatter for ultra-low power uplinks from wearable and implantable devices; In Proceedings of the 2012 ACM workshop on Medical communication systems; 6 pages; retrieved from the internet (http://conferences.sigcomm.org/sigcomm/2012/paper/medcomm/p1.pdf); Aug. 13, 2012.
Xu et al.; A novel mat-based system for position-varying wireless power transfer to biomedical implants; IEEE Transactions on Magnetics; 49(8); pp. 4774-4779; Aug. 2013.
Yeh et al.; Wirelessly powering miniature implants for optogenetic stimulation; Appl. Phy. Lett.; 103; 163701; 4 pages; Oct. 8, 2013.

* cited by examiner

AUTOFOCUS WIRELESS POWER TRANSFER TO IMPLANTABLE DEVICES IN FREELY MOVING ANIMALS

CROSS REFERENCE TO RELATED APPLICATIONS

This application claims the benefit of U.S. Provisional Appln. No. 61/991,266, titled "Autofocus Wireless Power Transfer to Implantable Devices in Freely Moving Animals", filed on May 9, 2014, which is incorporated herein by reference in its entirety.

STATEMENT OF GOVERNMENT SUPPORT

This invention was made with Government support under Contract NS080954 awarded by the National Institutes of Health. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure is generally related to fully implantable, wirelessly powered stimulators.

BACKGROUND

Practical and effective light delivery during behavioral modulation is a key challenge in applying optogenetics to understand and control neural function. Initial solutions to this problem have relied on tethered optical fiber-based systems, in which a fiber optic is inserted into the brain of an animal. Such systems exploit the stable nature of the brain-skull interface, enabling persistent optogenetic modulation of identified neural populations. These systems have been refined over the past decade, such as by allowing fiber rotation during animal movements using optical and electrical commutators and by improving the ease of attachment and detachment. These tethered systems nonetheless impose significant constraints on experimental design and interpretation, both by requiring investigators to handle and physically restrain animals to attach an optical fiber prior to behavioral testing, and by limiting the environments in which optogenetic experiments can be performed.

Recent efforts have been made to eliminate tethers by delivering light via wireless headmounted systems. In one design, a battery-powered, wirelessly-controlled device that delivers light through a thinned mouse skull with an LED. That system has subsequently been improved by decreasing its size, and was used to demonstrate motor activation using optogenetic stimulation of primary motor cortex. Another solution advanced wireless optogenetics through the use of a wirelessly powered system that removed the need for bulky batteries. Another approach developed a flexible, injectable LED-based system for optogenetic stimulation that was capable of stimulating deeper brain regions and could be powered by a head-mountable wireless power receiver.

These advances of wireless optogenetic technology, although trailblazing, have been limited by the mass and size of the devices. The reported wireless systems weigh 0.7 to 3 g (the mass of a mouse head is approximately 2 g). While the smallest wirelessly powered device weighs 0.7 g, it lacks remote-control. All previous devices are so large that they protrude several millimeters beyond the skin and cannot be left attached to the animal for prolonged periods of time. Head-mountable devices of this mass and size ultimately limit which central nervous structures can be targeted, and prohibit optogenetic control of the spinal cord or peripheral nervous system. Further, they hinder the animal's freedom of movement and behavior by preventing animals from entering small enclosures or engaging in normal social interactions with other mice.

No fully internal device has yet enabled optogenetic control of neural circuits.

SUMMARY OF THE DISCLOSURE

A light delivery system is provided, comprising a resonant cavity configured to generate electromagnetic energy and having a surface upon which an animal can be placed, and a wirelessly powered implantable device adapted to be implanted in the animal, the implantable device comprising a circuit board, a power receiving coil coupled to the circuit board and adapted to receive electromagnetic energy from the resonant cavity, a rectifier coupled to the circuit board and the power receiving coil and adapted to convert RF energy generated in the power receiving coil into a DC current, a micro-LED coupled to the circuit board and adapted to provide optogenetic stimulation to the animal.

In some embodiments, the implantable device is configured to be implanted on or near the animal's brain. In another embodiment, the implantable device is configured to be implanted on or near the animal's spinal cord. In an additional embodiment, the implantable device is configured to be implanted on or near nerve endings of one or more of the animal's limbs.

In one embodiment, the implantable device further comprises a conductive extension coupling the micro-LED to the circuit board.

In one embodiment, the implantable device is as small as 10 to 25 mm$^3$ in volume.

In another embodiment, the implantable device has a mass ranging from 20 to 50 mg.

A wirelessly powered implantable device adapted to be implanted in an animal is also provided, the implantable device comprising a circuit board, a power receiving coil coupled to the circuit board and adapted to receive electromagnetic energy from a resonant cavity, a rectifier coupled to the circuit board and the power receiving coil and adapted to convert RF energy generated in the power receiving coil into a DC current, and a micro-LED coupled to the circuit board and adapted to provide optogenetic stimulation to the animal.

In some embodiments, the implantable device is configured to be implanted on or near the animal's brain. In another embodiment, the implantable device is configured to be implanted on or near the animal's spinal cord. In an additional embodiment, the implantable device is configured to be implanted on or near nerve endings of one or more of the animal's limbs.

In one embodiment, the implantable device further comprises a conductive extension coupling the micro-LED to the circuit board.

In one embodiment, the implantable device is as small as 10 to 25 mm$^3$ in volume.

In another embodiment, the implantable device has a mass ranging from 20 to 50 mg.

In one embodiment, one or more outer turns of the power receiving coil can be bent at an angle with respect to one or more internal turns of the power receiving coil to compensate for rotation of the implantable device.

A power transmitter configured to transmit wireless energy to a power receiver is provided, comprising a resonant cavity, a flat surface positioned above the resonant cavity and comprising a surface lattice of subwavelength apertures, a plurality of monopole feeds disposed in the resonant cavity, and a signal generator configured to provide power to the plurality of monopole feeds to generate an evanescent field at the surface lattice that transmits wireless energy to the power receiver when the power receiver is brought into proximity with the surface lattice.

A method for stimulating an animal is provided, comprising the method steps of generating evanescent fields with a power transmitter, transmitting wireless energy from the power transmitter to a wireless device that is implanted in an animal passing through the evanescent fields, and stimulating the animal with the wireless device.

In some embodiments, the generating step comprises generating evanescent fields with one or more monopole feeds disposed in a resonant cavity of the power transmitter.

In one embodiment, the method further comprises allowing the animal to move on or around the power transmitter.

In another embodiment, the method further comprises enclosing the animal into or near the power transmitter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
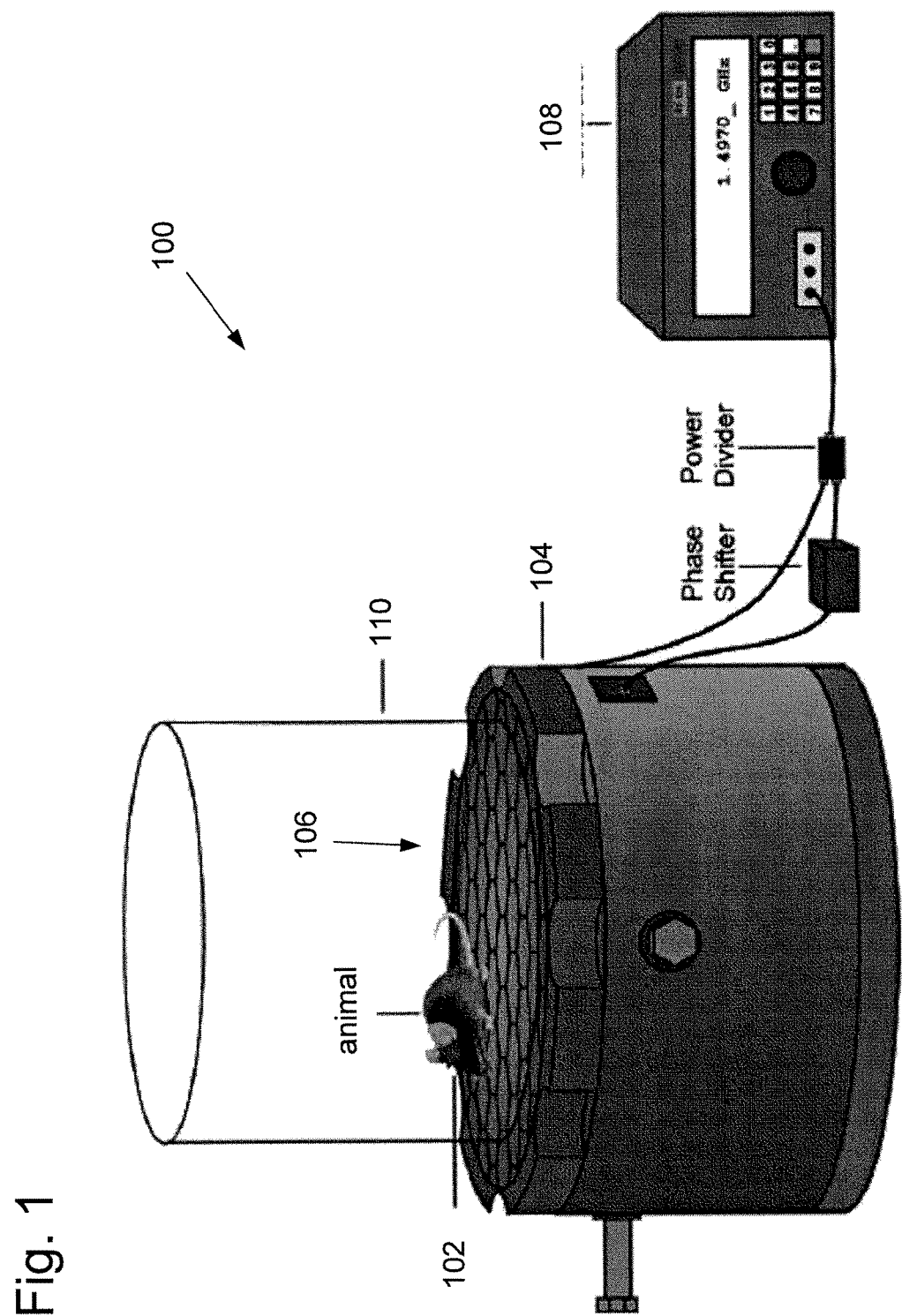
FIG. 1 illustrates one embodiment of a light delivery system configured to provide light delivery to an animal such as a mouse using wirelessly powered and fully internal implantable devices.

This disclosure describes a novel approach for investigating neuronal signaling. The approach described herein exploits high dielectric permittivity of biological tissue to tunnel energy to the implantable devices in animals, that is, it uses tissue to facilitate the coupling of energy from the transmitter to the implanted receiver. Wherever the animal is located, energy can be tunneled automatically to the implanted receiver.

To enable more sophisticated optogenetic manipulation of neural circuits throughout the nervous system with limited disruption of animal behavior, advances in light delivery beyond fiber optic tethering and large, head-mounted wireless receivers are required. This disclosure provides embodiments of easy-to-construct, implantable wireless optogenetic devices. In some embodiments, the implantable wireless devices can be as small as 20 mg, 10 mm$^3$, which is two orders of magnitude smaller than previously reported wireless optogenetic systems, allowing the entire device to be implanted subcutaneously. The implantable wireless devices of this disclosure can be powered with a radio-frequency (RF) power source and controller, and can be configured to produce sufficient light power for optogenetic stimulation with minimal tissue heating (e.g., less than 1 deg C.). While the specific embodiments described herein discuss optogenetic stimulation, in other embodiments the implantable devices can be configured to provide electrical stimulation. Also described herein are three specific adaptations of an implantable wireless device which allow for untethered optogenetic control throughout the nervous system (brain, spinal cord, and peripheral nerve endings) of living organisms such as mice. While description of the implantable wireless devices herein are made with respect to mice, it should be understood that the devices can be implanted in any living organisms, including humans.

This disclosure provides an easy-to-construct, fully internal device for wireless optogenetic stimulation of brain, spinal cord, or peripheral nerve endings that is two orders of magnitude smaller and lighter than any previously reported wireless optogenetic systems. The entire stimulator, including a power receiving coil, circuit, and light emitting diode (LED), can be as small as 10 to 25 mm$^3$ in volume, with a mass ranging from 20 to 50 mg depending on the target neural structure, and can be fully implanted beneath the skin of the animal or human. The small size of the stimulator allows for implantation in peripheral locations, such as limbs or the spinal cord, expanding the diversity of potential stimulation targets beyond the brain. When implanted in animals, such miniaturized wireless devices allow the animals to move more freely, within their own home-cage, through obstacles, into enclosures, and among other animals, and do not require the animal to be handled just prior to experiments. The implanted devices described herein can be built with readily available components and tools, and powered by a custom resonant cavity, which can be machined commercially, enabling adoption by the scientific community.

This disclosure also provides embodiments of a power transmitter that can include a microwave cavity resonant at a desired operating frequency, a hexagonal mesh top to leak the evanescent fields out of the cavity, and a plurality of orthogonal monopole feeds with 90 degrees phase differences creating circularly polarized waves. The power transmitter can be configured to transmit energy to a wireless device implanted in an animal supported by the hexagonal mesh top and passing through the evanescent fields. If there is no animal passing the mesh, the power transmitter merely emits evanescent fields so the energy leaked out to the air will be minimal. If there is an animal passing one or multiple cells of the mesh, due to the high dielectric property of biological tissue relative to air, energy will be extracted from the cavity through the evanescent fields to an implanted receiver in the animal.

FIG. 1 illustrates one embodiment of a light delivery system 100 configured to provide light delivery to an animal such as a mouse using wirelessly powered and fully internal implantable devices. The light delivery system 100 can comprise a wirelessly powered implantable device 102 implanted in an animal, such as a mouse. The device 102 can be powered and controlled using a resonant cavity 104 with a surface lattice 106 of hexagons and a plurality of monopole feeds (not shown) to couple electromagnetic energy to the tissue of an animal. A signal generator 108 can provide power to the monopole feeds of the resonant cavity 104. In one embodiment, the system can further include one or more phase shifters and/or power dividers between the signal generator and the resonant cavity. In some embodiments, the resonant cavity can comprise aluminum and can be approximately 21 cm in diameter and 15 cm in height. The surface lattice of hexagons can have a diameter of approximately 2.5 cm to couple electromagnetic energy at approximately 1.5 GHz to the tissue of the animal. The animal can be enclosed into or near the resonant cavity 104 with an enclosure 110, such as a glass cover.

When an animal such as a mouse is placed on the lattice, strong field confinement occurs within the mouse due to a volume resonance determined by the dielectric properties and physical dimensions of the animal. Conventional inductive systems transfer energy through direct coupling between one coil and another. In this system, however, the resonant interaction between the cavity and the animal mediates power transfer to the implanted device. Because energy is concentrated in the animal at all positions on the lattice, the power transfer is self-tracking and efficient enough to power the wireless implant. Unlike radiative alternatives to the resonant cavity, such as highly directional antennas, here tracking algorithms are not required to maintain performance within the cavity.

Figure 2A:
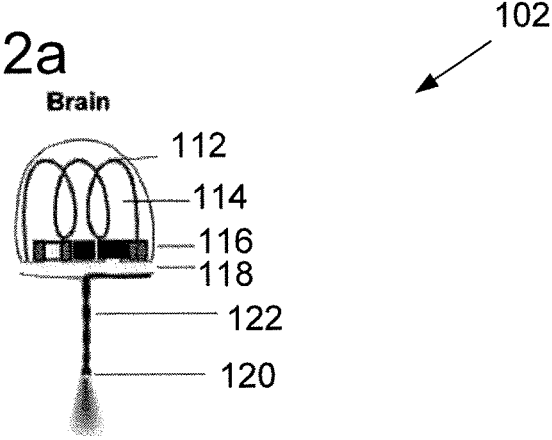
FIGS. 2a-2c illustrate various embodiments of fully internal, wirelessly powered implantable devices configured to emit light in the brain, spinal cord, and at peripheral nerve endings of a subject.
Figure 2B:
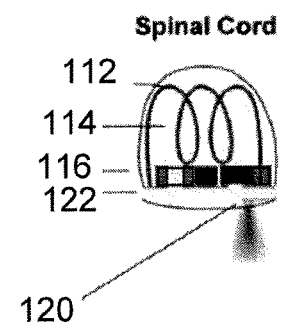
Figure 2C:
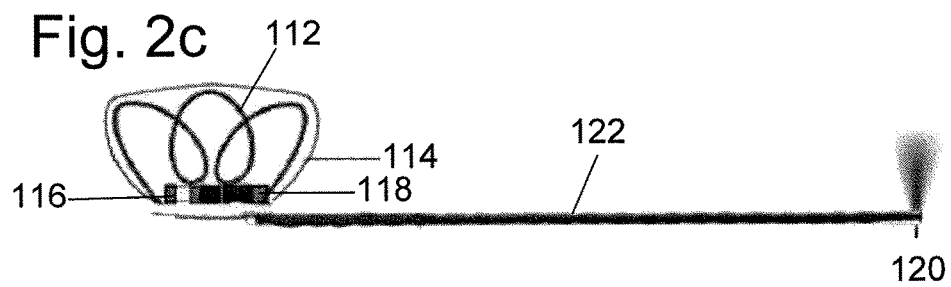

FIGS. 2a-2c illustrate various embodiments of fully internal, wirelessly powered implantable devices configured to emit light in the brain, spinal cord, and at peripheral nerve endings of a subject. Three versions of the implantable device are described and illustrated which target three different neural structures, specifically the premotor cortex of the brain (FIG. 2a), the dorsal horn of the spinal cord (FIG. 2b), and peripheral nerve endings of the heel of a limb (FIG. 2c). Each implantable device 102 can include a power receiving coil 112 disposed in an acrylic potting material 114, coupled to a rectifier 116 and a circuit board 118. The implantable devices can be configured to deliver light to the subject with a micro-LED 120. In the embodiments of FIGS. 2a and 2c, the micro-LED 120 can be coupled to the circuit board 118 with an extension 122, which can comprise a pair of magnetic wires. In one specific embodiment, the extension 122 can comprise a pair of 250 µm diameter magnetic wires. In the embodiment of FIG. 2b, the micro-LED 120 can be coupled directly to the circuit board to avoid penetrating the spinal cord.

Each implantable device of FIGS. 2a-2c can be implanted entirely under the skin of the animal, with a negligible change to the animal's profile. The circuit board and power receiving coil can be configured to deliver current to the micro-LED. In some embodiments, the micro-LED can be a blue LED designed to activate channelrhodopsin (ChR2). Acrylic encapsulation of the implant resists biological degradation and electrically insulates the circuitry. Due to the concentration of electromagnetic energy from the resonant cavity, and the low gigahertz frequencies used, power receiving coils can be used to harvest power in the implantable devices that are significantly smaller (e.g., 1.6 mm diameter) than conventional inductive systems.

Figure 3A:
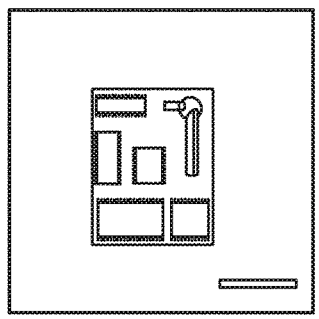
FIGS. 3a-3l illustrate step-by-step construction of the implantable devices of this disclosure.
Figure 3B:
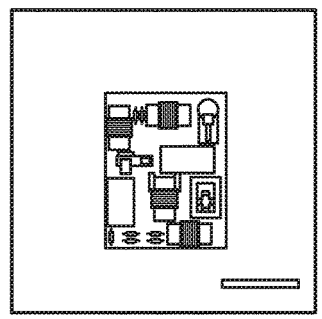
Figure 3C:
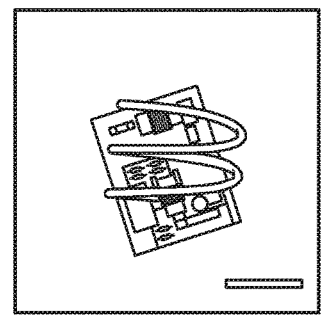
Figure 3D:
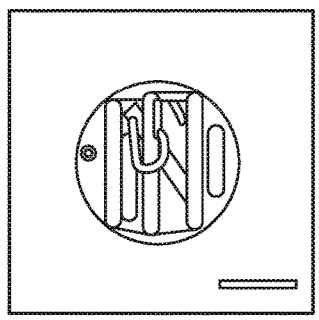
Figure 3E:
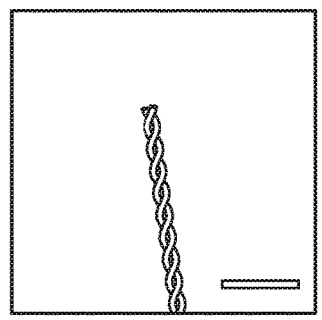
Figure 3F:
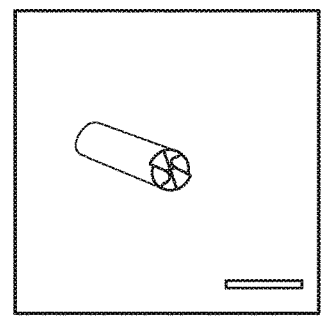
Figure 3G:
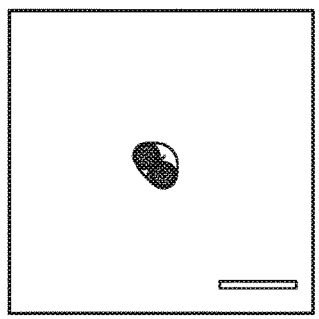
Figure 3H:
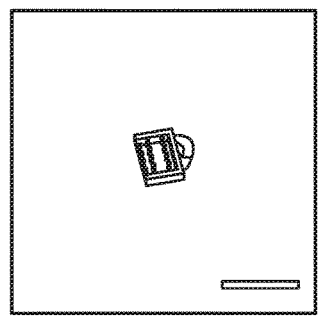
Figure 3I:
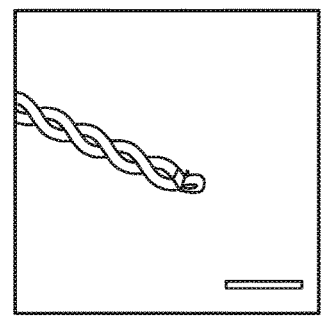
Figure 3J:
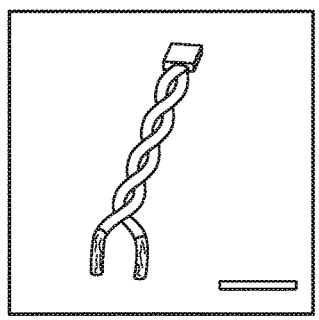
Figure 3K:
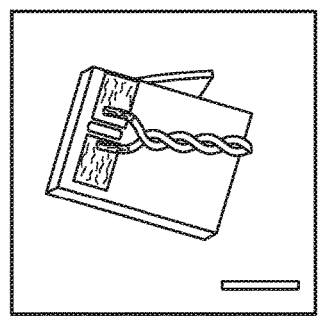
Figure 3L:
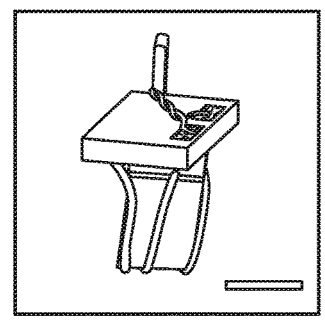

FIGS. 3a-3l illustrate step-by-step construction of the implantable devices of this disclosure. To give a reference for scale, the black scale bars in the figures measure 1 mm, and the white scale bars in the figures measure 0.5 mm. FIG. 3a shows the printed circuit board (PCB) cut to size, and solder paste applied to the metal traces on the PCB. FIG. 3b shows the surface-mount devices (SMD) bonded with reflow soldering. FIG. 3c illustrates the power receiving coil soldered to the PCB. In one embodiment, the power receiving coil can be constructed by wrapping wire around appropriately sized tubing and cutting the wires with wire cutters. The coil for the brain and spinal cord implants can comprise of 3 turns of 34 gauge magnet wire with an inner diameter of approximately 1.6 mm. The coil for the peripheral implant can have an approximate 1.8 mm diameter and the outer turns of the coil can be bent 45 degrees with respect to the internal turns of the coil to compensate for the rotation of the implant along the axis of the coil. In FIG. 3d, the coil and SMD components were stabilized with acrylic. FIG. 3e shows the extension formed from a pair of twisted 36 AWG wires. In FIG. 3f, ends of the twisted wires were separated by 70 µm. FIG. 3g illustrates solder paste applied to the tips of the bared wires. In FIG. 3h, the micro-LED is shown placed on the ends of the wires. In one embodiment of the brain implant, the micro-LED can be mounted downwards to deliver light to target regions within the brain. Thus, the exposed copper at the end of the two wires can form two conductive pads for the terminals of the micro-LED. For the peripheral implant, the micro-LED can be mounted to the side of the extension to deliver light through the skin. In this specific embodiment, the coating on a 1-mm section on the sides of the wires near the tip is removed to form two conductive pads. The twisted magnet wires can then be clamped vertically to a soldering wire holder. In FIG. 3i, the extension is shown positioned for reflow with a butane torch, and in FIG. 3j the extension is cut to the desired length and tested for polarity. In FIG. 3k, the extension is illustrated soldered to the bottom of the PCB. Finally, in FIG. 3l, the extension is shown bent to the desired angle and a final coat of acrylic was applied.

The implantable device of FIG. 2a can be rigidly cemented to the skull or the subject animal, with the short extension and downward facing micro-LED penetrating the surface of the brain, similar to traditional optical fiber implants. An extension is not included in the implantable device of FIG. 2b to minimize damage to the spinal cord. Instead, the micro-LED in that embodiment is mounted directly on the circuit board to avoid penetrating the cord. The peripheral implant of FIG. 2c can be configured to deliver light subcutaneously using a long, flexible extension (i.e., longer than the extension of the FIG. 2a embodiment). Peripheral implants change spatial orientation relative to the cavity more than central ones during the natural course of locomotion. Due to this variability in orientation of the peripheral implant, the individual turns of the power receiving coil can be set to be non-parallel, thus minimizing orientation-related power fluctuations.

The wirelessly powered implantable devices described herein can generally comprise two main parts. The first part of the device is the power receiver including the power receiving coil and the rectifier. The power receiving coil is configured to extract RF energy coupled from the resonant cavity to the target animal. The rectifier is configured to convert the RF energy into DC current. In one embodiment, the rectifier can be implemented by a two-stage voltage doubling circuit using Schottky diodes. All rectifier and power receiving coil components can be bonded to a circuit board made of Roger PCB material for its flexibility for ease of cutting. The second part of the device is the light delivery portion, routing the DC current from the rectifier to a micro-LED designed to be implanted directly at the stimulation site.

As described above, for the spinal cord implant (FIG. 2b), the LED can be directly attached to the bottom of the PCB. For the brain and peripheral implants (FIGS. 2a and 2c, respectively), a pair of magnet wires can be used to route the DC current from the rectifier to the micro-LED, which can be attached at the tip of the wires. In some embodiments, the diameter of this extension is about 250 μm.

Figure 4:
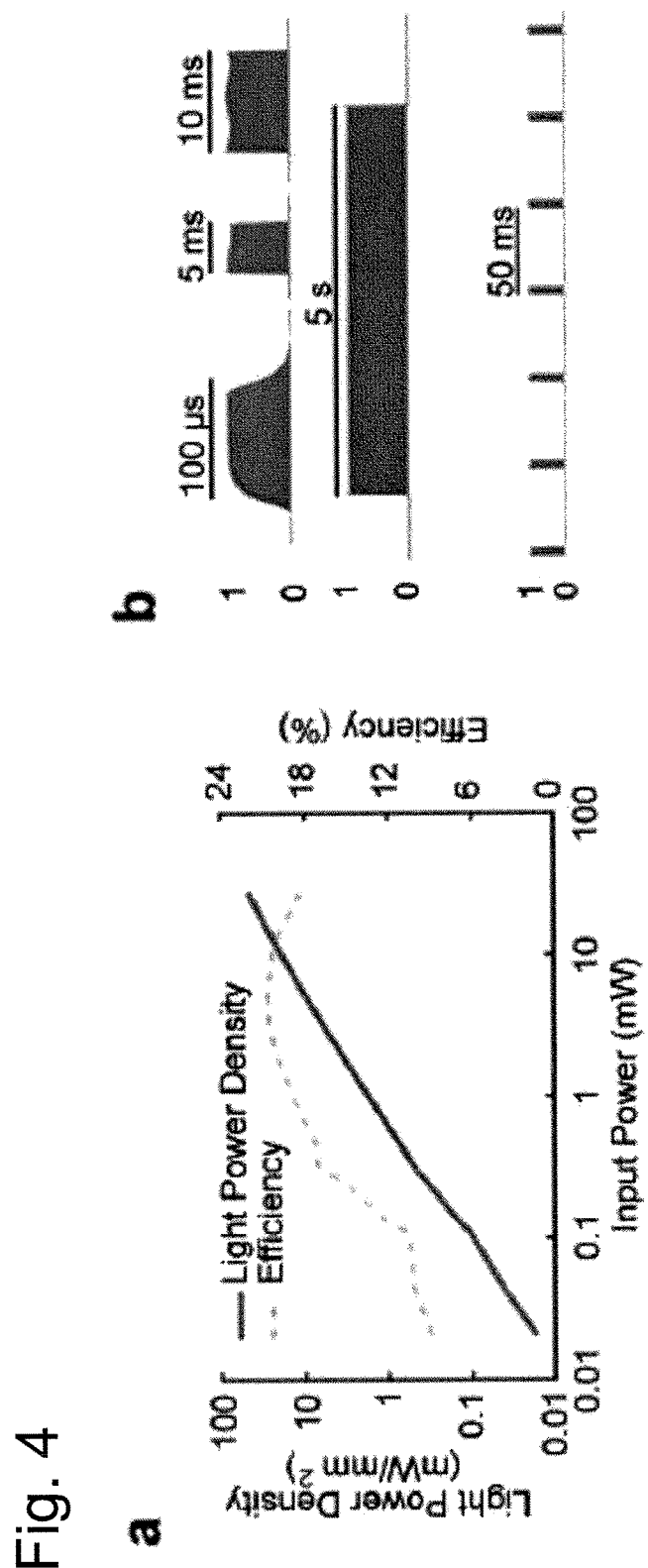
FIG. 4a is a diagram showing how light power density and efficiency of the LED are each a function of the power supplied to the micro-LED.
FIG. 4b shows the fidelity of light output for step-function pulses of various pulse widths.
FIG. 4c illustrates a calculated light power density across the width of the behavioral area above resonant cavity.
FIG. 4d-e illustrate the heating of tissue directly adjacent to the implanted micro-LED.
Figure 4:
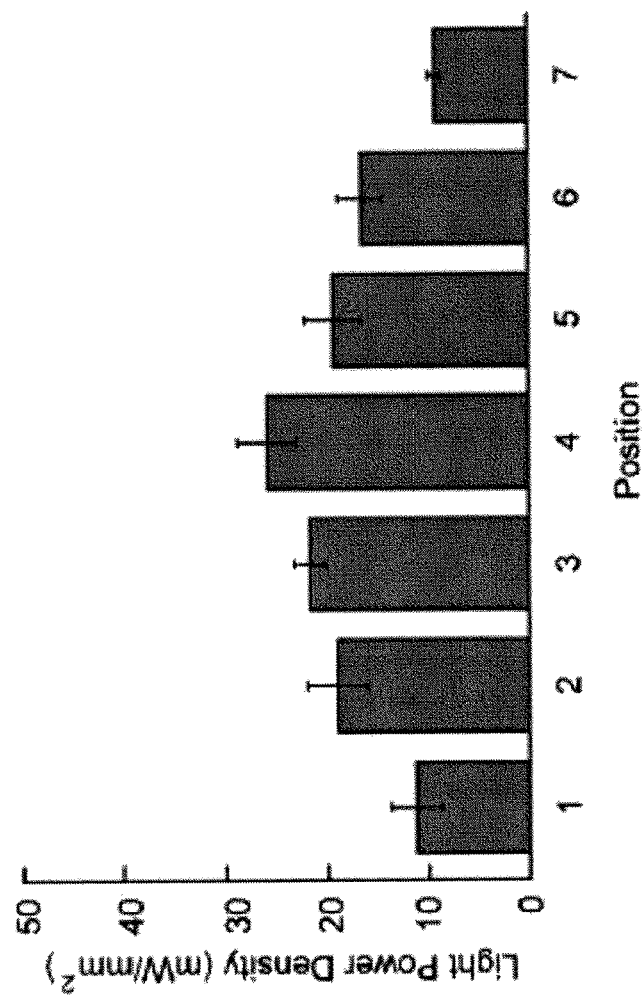
Figure 4:
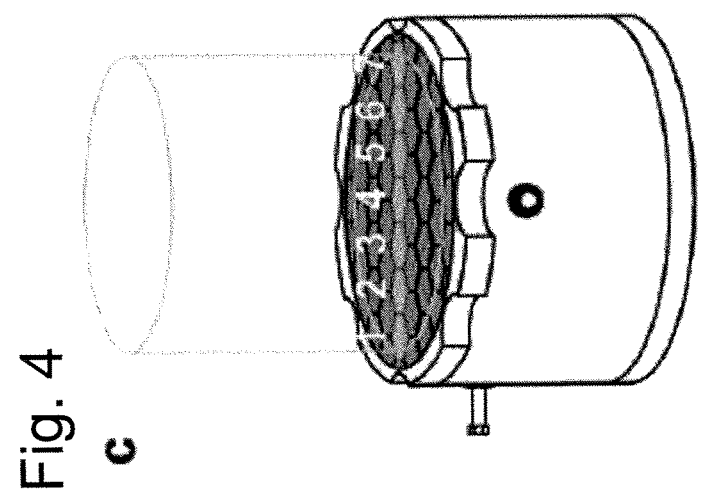
Figure 4:
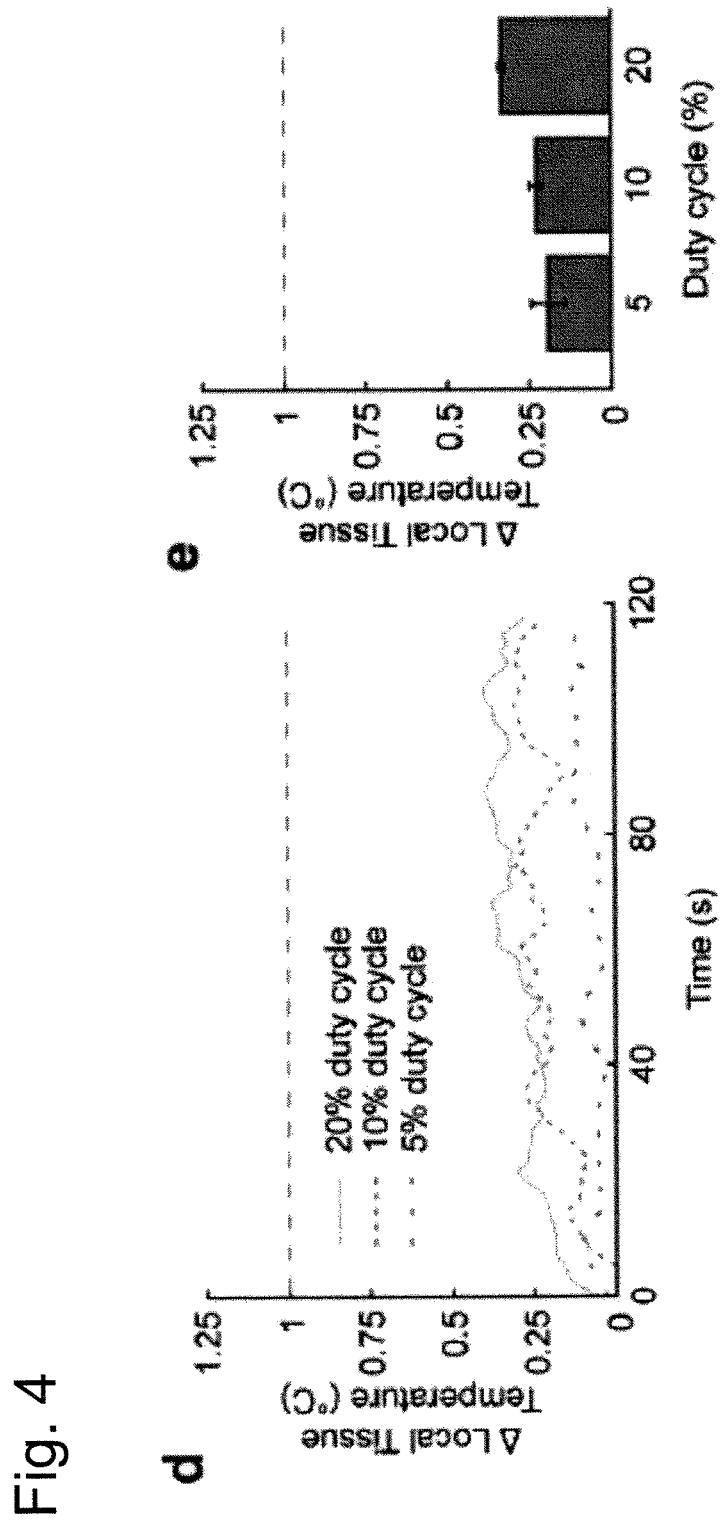

The implantable devices described herein provide light power densities and pulse characteristics suited for optogenetic stimulation without generating excessive heat. FIG. 4a is a diagram showing how light power density and efficiency of the LED are each a function of the power supplied to the micro-LED. Here, power is supplied in the wireless implant by captured and rectified energy. Light power density can be adjusted by varying the input power to the resonant cavity. To characterize this, the emitted light power from the micro-LED can be measured when supplying the micro-LED with a known current via wired circuitry. The light power density can then be estimated as a function of input power to the micro-LED, shown in FIG. 4a. Over the range of light power densities suitable for optogenetic stimulation (1 to 20 mW/mm2), the micro-LED of the present disclosure is efficient (emitted light power/input power=19%).

FIG. 4b shows the fidelity of light output for step-function pulses of various pulse widths. The relative transient intensities (a.u.) for 100 μs, 5 ms, 10 ms, and 5 s pulses are shown. In some embodiments, pulses as short as 100 μs can be delivered without decay in peak relative power. Towards the bottom of FIG. 4b, consecutive 5 ms pulses are shown, indicating no loss of light output fidelity with consecutive pulses.

FIG. 4c illustrates a calculated light power density across the width of the behavioral area above resonant cavity. The left side of FIG. 4c shows the resonant cavity with positions 1-7 spanning across the cavity, and the right side of FIG. 4c shows the light power density at positions 1-7 of the cavity.

FIG. 4d illustrates the heating of tissue directly adjacent to the implanted micro-LED. More specifically, FIG. 4d shows the change in local tissue temperature resulting from a wired micro-LED being inserted into brain, operating with a light power density of 40 mW/mm2 at 5%, 10%, and 20% duty cycles (5 ms pulse width; 10 Hz, 20 Hz, and 40 Hz frequencies, respectively). FIG. 4e shows that the temperature change resulting from optogenetic stimulation with micro-LEDs of the present disclosure stabilizes below levels typically associated with neural damage (1 degree C.).

Efficient micro-LEDs lead to minimal temperature increases in vivo. The local temperature of tissues can increase at sites of light stimulation due to the absorption of photons by tissue and heat dissipation of the micro-LED. This is concerning, as such heating could result in tissue damage or artifactual changes in neural activity (i.e., not optogenetically driven). The implantable devices of the present disclosure are configured to avoid this concern by using highly efficient micro-LEDs that produce sufficient light power for optogenetic stimulation but result in minimal heating of the surrounding tissue. The optogenetic stimulation can result in a small but consistent general whole body heating in the subject, on the order of 0.5 degrees C. greater than control, of the animal due to absorption of RF energy from the concentrated electromagnetic field created by the power source and resonant cavity. For example, normal mouse body temperature varies between 34 degrees C. and 39 degrees C., and during testing the electromagnetic field did not cause fluctuations outside of this temperature range.

Figure 5:
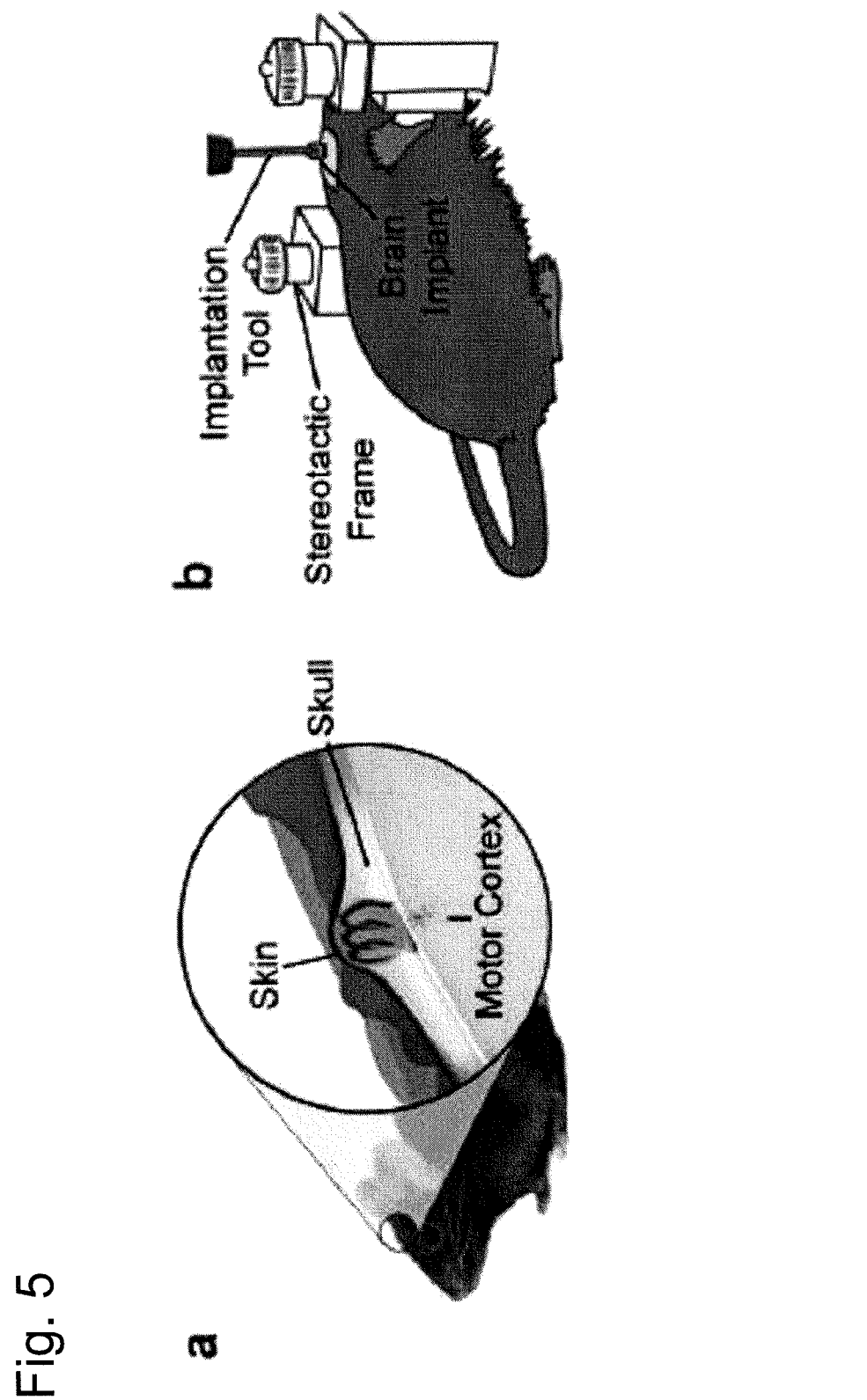
FIGS. 5a-b show wireless implantable device of FIG. 2a implanted into of the brain of a rodent and configured for wireless optogenetic stimulation of the premotor cortex.
FIG. 5c shows how motor stimulation of the left motor cortex can cause circling behavior with increase in average speed.
FIGS. 5d-f show representative traces of mouse movement during on-off cycles.
Figure 5:
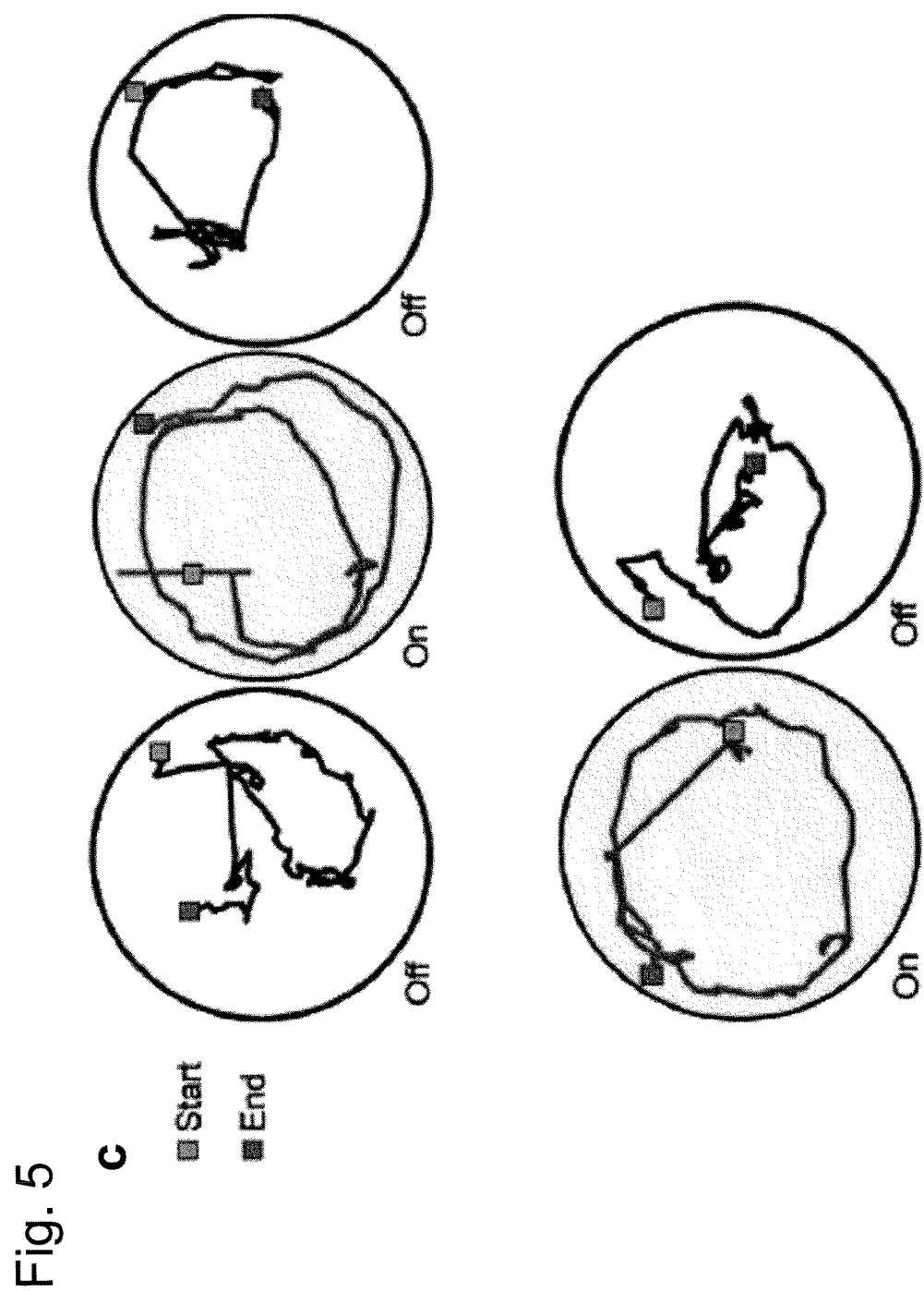
Figure 5:
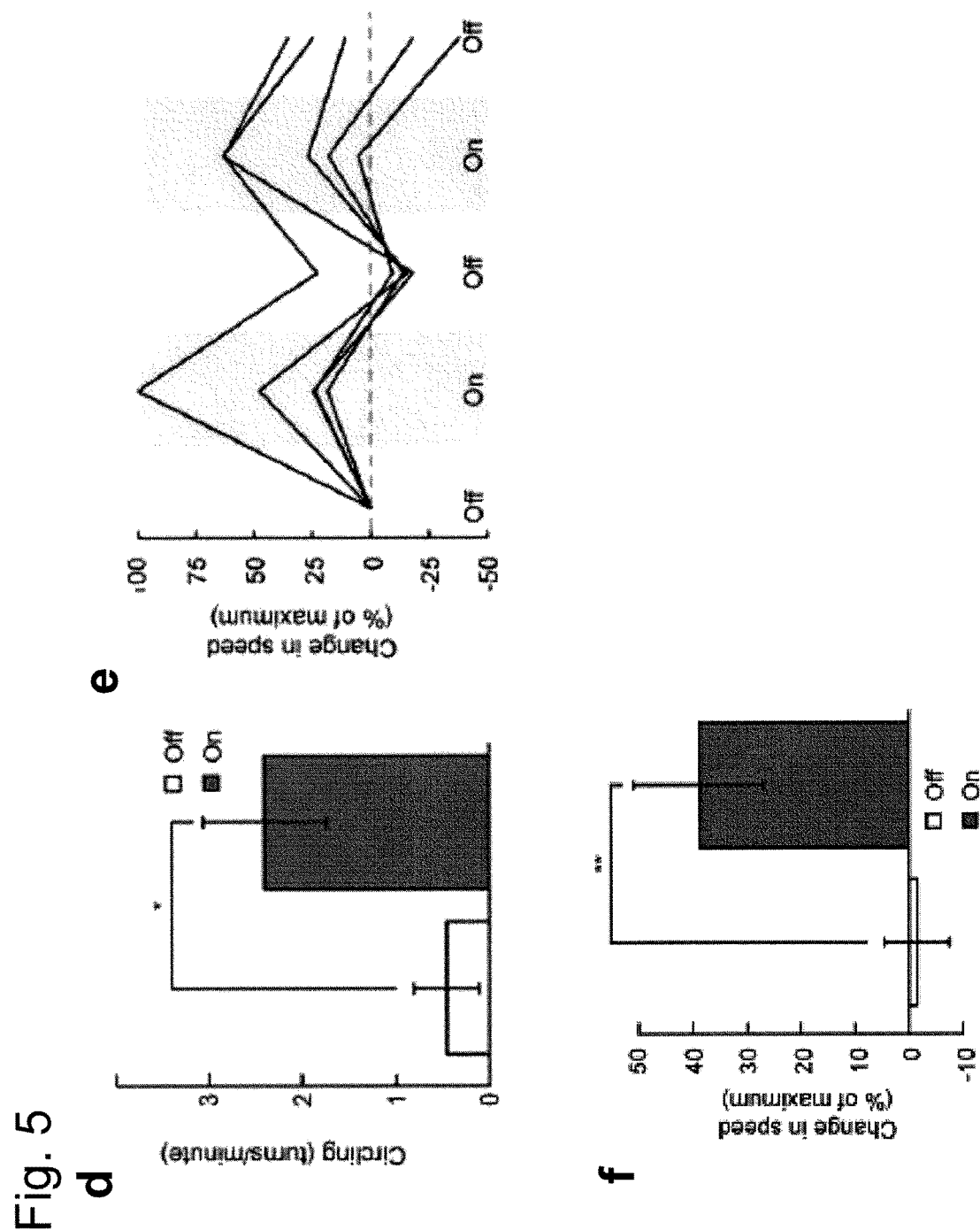

FIGS. 5a-b show wireless implantable device of FIG. 2a implanted into of the brain of a rodent and configured for wireless optogenetic stimulation of the premotor cortex (M2). As shown in FIG. 5a, the device can be implanted such that the circuit board and coil are above the skull and below the skin of the animal, and the micro-LED at the tip of the extension is inserted into the brain directly above motor cortex. FIG. 5b illustrates how implantation can be performed using a stereotactic frame with implantation tool bonded to the device. The extension and micro-LED of the device can be inserted into the brain of the mouse, and the coil and board can be bonded to the skull. The implantation tool can then be removed from device, and the skin of the animal can be sutured over the device. In one embodiment, the total implantation time can be approximately 30 minutes.

FIG. 5c shows how motor stimulation of the left motor cortex can cause circling behavior with increase in average speed. In one embodiment, the animal was optogenetically stimulated with 5 ms pulses at 20 Hz. Stimulation can be wirelessly controlled in discrete (e.g., 20-second) on-off cycles. Representative traces of mouse movement during on-off cycles are shown. In one example, the circling rate of mice increases from 0.46 turns/minute to 2.4 turns/minute, (n=5 ChR2+ mice, P=0.0148, effect size=0.633), as shown in FIGS. 5d-f. The mean speed of mice, normalized by each mouse's maximum speed, increased by 40% compared to no optogenetic stimulation, and this behavior was replicated for multiple test subjects. The cohort mean shown in FIG. 5f was tested to be (n=5 ChR2 mice, P=0.0025, effect size=2.4).

Figure 6:
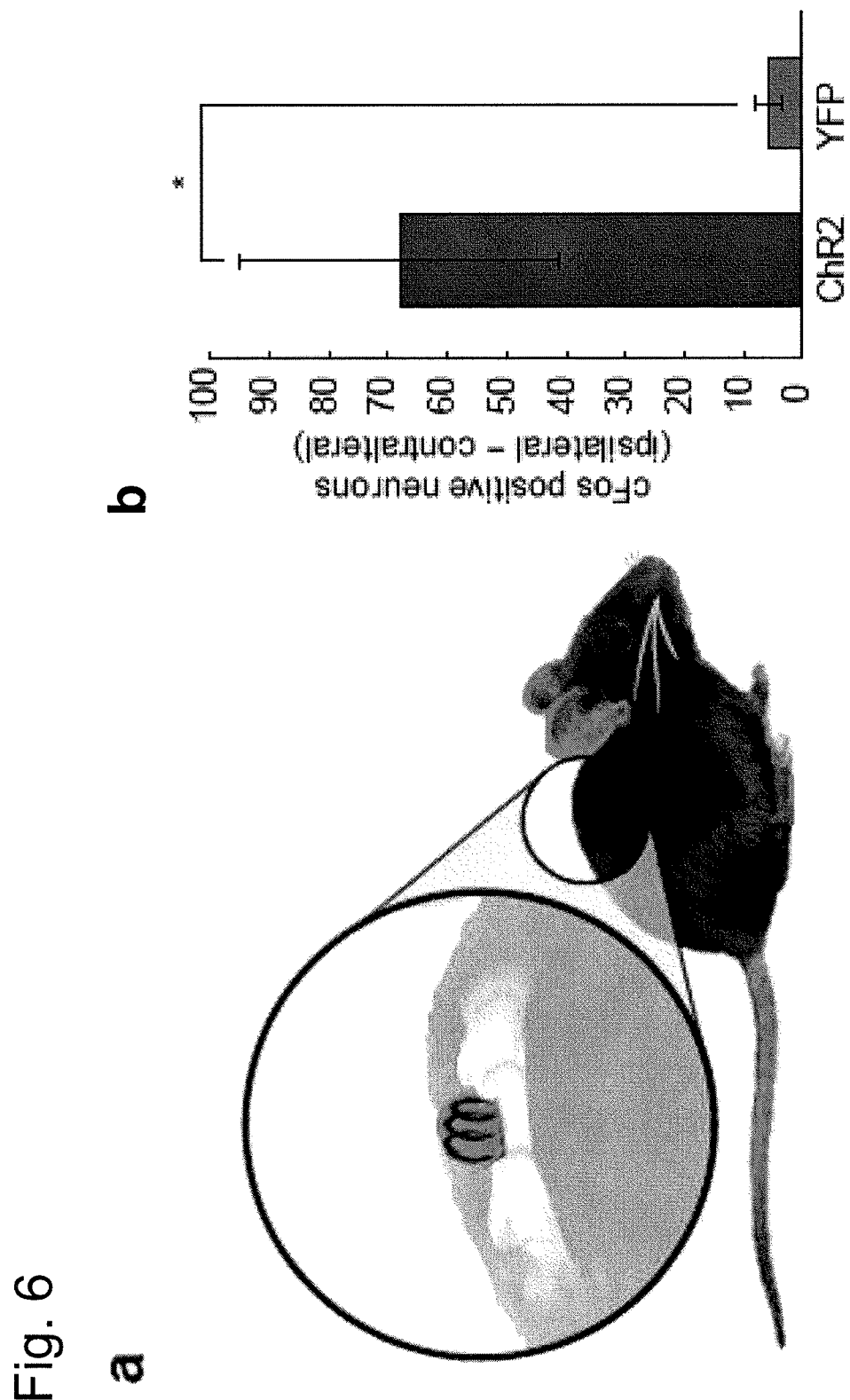
FIG. 6a shows the device of FIG. 2b implanted on the right side of the dorsal surface of a vertebra in a mouse.
FIG. 6b is a chart showing stimulation of the spinal cord.

The implantable devices of the present disclosure can also be used to stimulate nerve cuffs and optical fibers to control spinal cord and peripheral nerve circuits in animals such as rodents. The small size of the wireless implants described herein allows for easy targeting of neural structures outside of the brain, such as the spinal cord, without affecting locomotion. The wireless implantable devices described herein can be configured to stimulate ChR2-expressing, unmyelinated nociceptors at the spinal cord in freely moving animals. FIG. 6a shows the device of FIG. 2b implanted on the right side of the dorsal surface of a vertebra in a mouse. A small hole can be drilled through the vertebra to provide a window for light delivery to the spinal cord (e.g., to L3/L4 of the spinal cord). FIG. 6b is a chart showing stimulation of the spinal cord (10 Hz frequency, 10 ms pulse width, 10 mW/mm2 light power density). ChR2+ mice show increased unilateral c-Fos expression during light stimulation compared to YFP+ mice (n=6 ChR2+ mice, 7 YFP+ mice, P=0.02, effect size=1.5).

Figure 7:
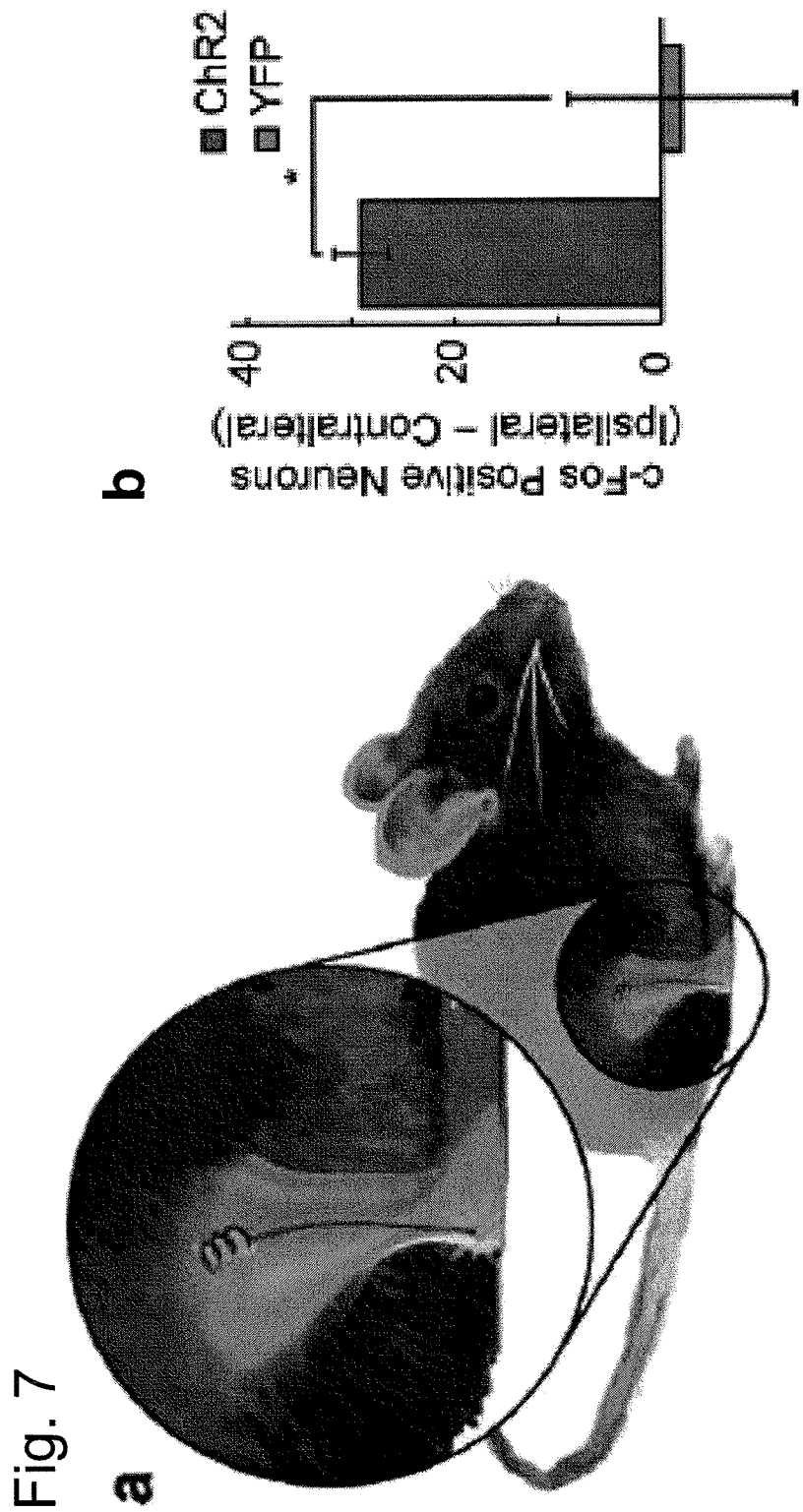
FIG. 7a shows the device of FIG. 2c implanted subcutaneously adjacent to the triceps surae muscles of a mouse with the micro-LED of the device routed to the heel.
FIG. 7b shows quantification of c-Fos expression that confirms unilateral activation of ChR2 after optogenetic stimulation.
FIG. 7c illustrates the movement of mice allowed to explore a two-chamber place aversion setup in which one floor was resting directly above the resonant cavity.
FIGS. 7d-f are charts showing that the ChR2-expressing mice spent significantly less time in the resonant cavity chamber than the non-resonant cavity chamber compared to control YFP-expressing mice.
Figure 7:
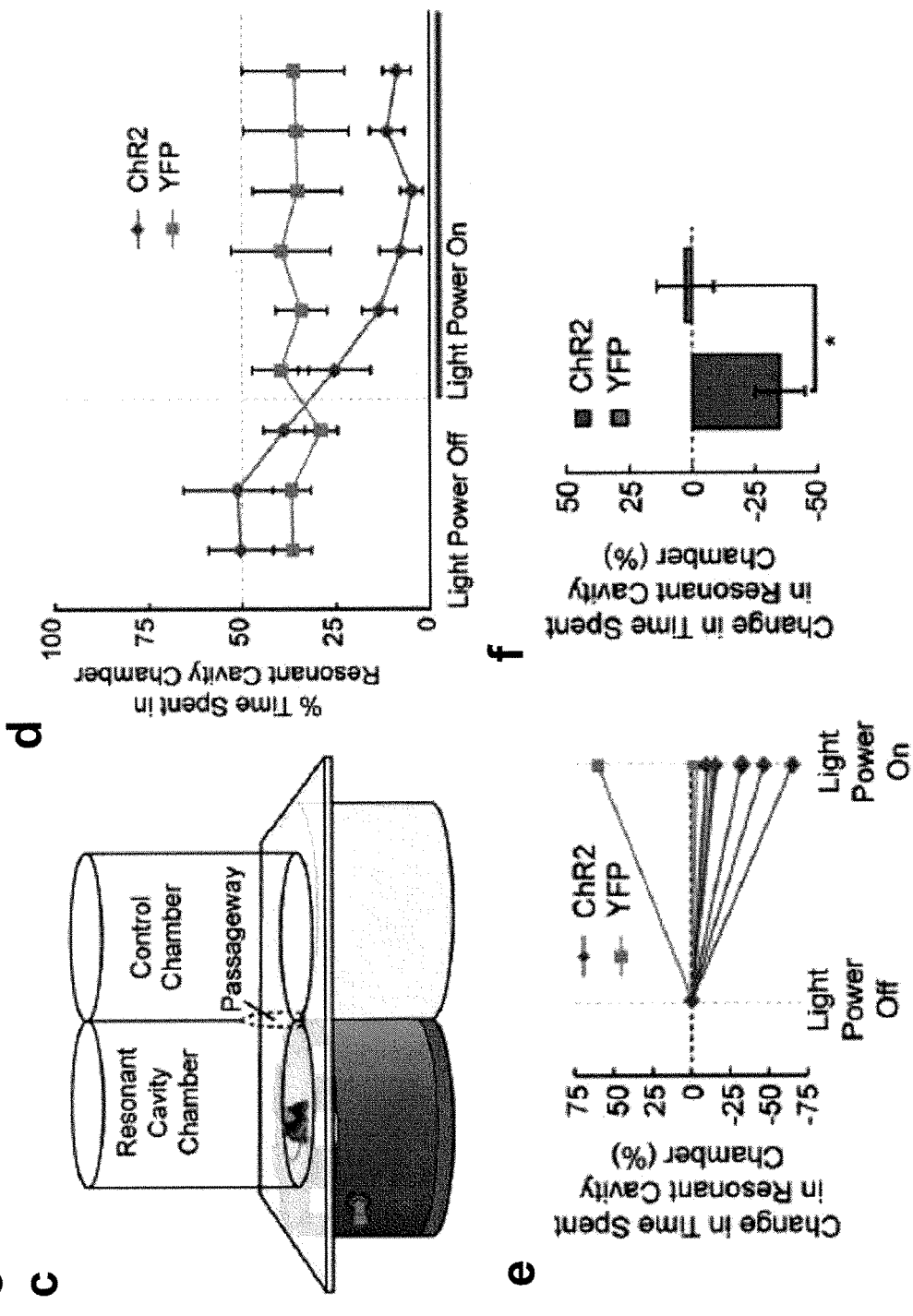

The implantable devices of the present disclosure can also be used to stimulate peripheral nerve endings. FIG. 7a shows the device of FIG. 2c implanted subcutaneously adjacent to the triceps surae muscles of a mouse with the micro-LED of the device routed to the heel. FIG. 7b shows quantification of c-Fos expression that confirms unilateral activation of ChR2 after optogenetic stimulation (e.g., 10 minute stimulation at 10 ms, 10 Hz, 10 mW/mm2). Unilateral c-Fos expression is significantly greater in ChR2+ mice compared to YFP controls (n=3 ChR2+ mice, n=2 YFP+ mice, P=0.04, effect size 2.22).

To demonstrate the utility of the wirelessly powered implants in studying operant behavior, mice were allowed to freely explore a two-chamber place aversion setup in which one floor was resting directly above the resonant cavity, as shown by FIG. 7c. After a 10-minute power-off habituation to the environment, mouse location within the two chambers was measured for 10 minutes followed by 15 minutes with the implant wirelessly powered on. The ChR2-expressing mice spent significantly less time in the resonant cavity chamber than the non-resonant cavity chamber compared to control YFP-expressing mice, as illustrated in FIGS. 7d-f. (n=5 ChR2 mice, 6 YFP mice, P=0.039, effect size=1.33).

The a miniature, light-emitting implants described herein can safely and effectively stimulate neurons in the brain, spinal cord, and peripheral nervous system with a micro-LED. This optogenetic system permits untethered animal movement in a diverse array of behavioral testing environments and has greatly reduced mass and volume in order to minimize interference with natural animal behavior.

Care should be taken when modifying this device with less efficient LEDs or when driving the blue LED with higher powers than reported here; increased power will increase both general heating of the animal by the RF field as well as local tissue heating at the LED, potentially beyond acceptable thermal thresholds. Also, it is important to consider how light power varies as a function of device orientation and position above the resonant cavity. A smaller enclosure can also reduce the power variability, although the reported system was sufficient to elicit reliable optogenetic control of behavior. Circuitry designed to regulate the output power in future iterations of this technology could provide more constant power.

In some embodiments, the implantable devices described herein can include sensing features and closed-loop control, as well as multiple light colors to match the vast array of available spectrum-sensitive opsins. Many other targets, including deeper regions of the brain, other peripheral nerves, nerve plexuses, and ganglia can also be targeted with this wireless technology. The resonant cavities can also be further designed to decrease variability in field strength, to allow for animal behavior in different shaped enclosures, to account for animal behavior tests in water, which has different dielectric properties than air, and to allow for optogenetic stimulation in larger mammals.

The small size and mass of this optogenetic system may enable the development of new optogenetics experiments with very little modification of the core technology, including chronic optogenetic stimulation of mice in their homecage, stimulation while navigating constricting obstacles, simultaneous stimulation of multiple, socializing animals, simultaneous stimulation of multiple neural targets in the same animal, and stimulation of deep neural targets outside of the brain, for example, branches of the vagus nerve or components of the enteric nervous system. This optogenetic system simplifies light delivery and paves the way for more natural behavior during optogenetic experiments.

Wireless power transfer enables electronics to be continuously powered within a defined electromagnetic region. Techniques for power transfer through biological tissue are generally based on inductive coupling, which relies on the exchange of energy between an implanted coil and an external coil through a quasi-static magnetic field. The efficiency of power transfer can be substantially enhanced by operating the coils at simultaneous resonance, but the efficiency remains limited for coils with highly asymmetric sizes. As a result, wireless systems demonstrated prior to the present invention have required large power harvesting stages that are mounted on the head of an animal subject. Even then, tissue heating due to exposure to electromagnetic fields remains an important problem.

To allow natural behavior, particularly with multiple subjects, efficient power transfer to fully-implanted electronic devices is required. In this disclosure, an alternative approach is disclosed in which energy is extracted from a cavity resonator by the animal subject. Power can be transferred to highly miniaturized electronic devices within a region sufficiently large to allow freely moving behavior. Due to the low power requirements for most electronic functions, power sufficient for most experimental tasks can be delivered under safe exposure levels.

Figure 8:
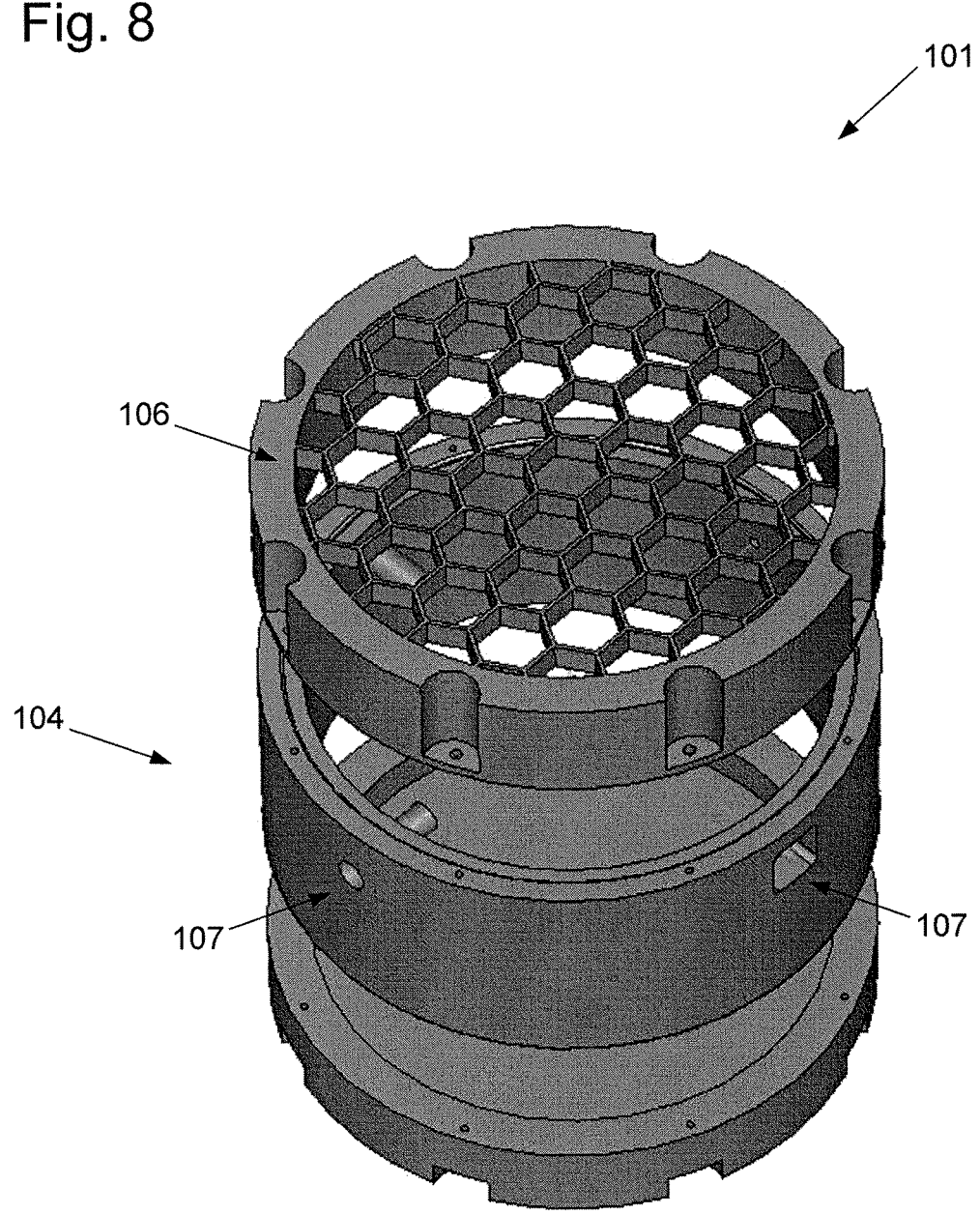
FIG. 8 shows one embodiment of a power transmitter comprising a resonant cavity and a surface lattice of subwavelength structures.

FIG. 8 shows a power transmitter 101 comprising cylindrical resonant cavity 104 in air with one of the flat surfaces replaced by a conductive mesh or surface lattice 106 of subwavelength apertures. The resonant cavity can further include a plurality of monopole feeds 107. Due to the subwavelength dimensions of the apertures, radiative energy transported out of the resonant cavity is minimal, while an evanescent field is formed at the surface of the mesh. At microwave frequencies, dispersion results in high dielectric permittivity values for nearly all types of biological tissue. As well-defined dielectric volumes, small animals support distinct electromagnetic modes. When the subject is brought in close proximity to the surface lattice, modes are coupled through the evanescent field, allowing energy to tunnel from the resonant cavity into the subject.

The energy extraction process is described by the coupled-mode equations:

$$\dot{\alpha}_1(t)=(-i\omega_1-\gamma_1)\alpha_1+\kappa\alpha_2+F \quad (1)$$

$$\dot{\alpha}_2(t)=(-i\omega_2-\gamma_2)\alpha_2+\kappa\alpha_1 \quad (2)$$

where $\alpha_1$ and $\alpha_2$ are the mode amplitudes, defined such that the energy in the objects are given by $|\alpha_1|^2$ and $|\alpha_2|^2$. Here, $\omega_1$ and $\omega_2$ are the resonant frequencies of the resonant cavities, $\kappa$ the coupling coefficient, and $F$ the driving force provided to the initial resonant cavity. In absence of the tissue volume, the steady-state amplitude has a time dependency of $\exp(-i\omega_1 t - \gamma_1)$.

To examine the coupling between the source resonator and the tissue, $\kappa$ is solved for by describing the fields in the source and the tissue by their normalized field patterns $e_1$ and $e_2$ respectively, assuming that the total field in the system is given by the superposition:

$$E = \alpha_1(t)e_1 + \alpha_2(t)e_2. \quad (3)$$

Normalization is achieved by finding the field value over the summed field intensities over the space:

$$e_n = \frac{E_n}{\int d^3 r |E_n|^2} \quad (4)$$

The rate of change of the energy in the tissue as a result of coupling can be written as:

$$\frac{d}{dt}|a_2|^2 = -\gamma_2 |a_2|^2 + \kappa a_1 a_2^* + \kappa^* a_2 a_1^*. \quad (5)$$

The evanescent field outside the source resonant cavity induces a polarization current in the tissue given by:

$$j\omega P_{21} = j\omega(\epsilon_2 - \epsilon_0)\alpha_1 e_1 \quad (6)$$

where the term $\epsilon_2 - \epsilon_0$ accounts for the polarization current $j\omega\epsilon_0 P_{21}$ in air.

Over the tissue volume, the transferred energy is given by the equation:

$$\frac{d}{dt}|a_2|^2 = \frac{1}{4}\int_{tissue} j\omega P_{21} \cdot a_2^* e_2^* dv \quad (7)$$

$$= \frac{1}{4}\int_{tissue} j\omega(\epsilon_2 - \epsilon_0)a_1 a_2^* e_1 \cdot e_2^* dv \quad (8)$$

A comparison of (4) and (7) yields the coupling coefficient:

$$\kappa = \frac{\frac{1}{4}\omega \int_{tissue}(\epsilon_2 - \epsilon_0)e_1 \cdot e_2^* dv}{\frac{1}{2}\int_{tissue}\epsilon_2 |e_2|^2 dv} \quad (9)$$

The power transfer efficiency to the tissue is given by:

$$\eta = \frac{P_{tissue}}{P_{all}} = \frac{\gamma_2 |a_2|^2}{\gamma_1 |a_1|^2 + \gamma_2 |a_2|^2 + 2\kappa \mathrm{Re}\{a_1 a_2\}}. \quad (10)$$

The space of suitable dimensions for a cylindrical cavity resonator, supporting only the lowest order ($TM_{110}$) mode, was established by the following equation:

$$\omega_{nml} = \frac{c}{\sqrt{\mu_r \epsilon_r}}\sqrt{\left(\frac{p_{nm}}{r}\right)^2 + \left(\frac{l\pi}{h}\right)^2} \quad (11)$$

where n, m, and l represent the number of half-period variations along the x, y, and z directions. The $p_{nm}$ are the corresponding roots described by a set of eigenvalues corresponding to the $TM_{nm}$ modes of a cylindrical waveguide. Given the set of possible heights, h, and radii, r, one specific embodiment comprises a h=14.5 cm and r=10.5 cm. The top of the metallic resonant cavity can be a high-density hexagonal mesh. Because the dimensions of the unit cell are subwavelength, radiation from the top is minimal, although the quality factor Q noticeably decreases with increasing grid size. As such, the aperture dimensions of the hexagonal grid can be chosen to optimize the resonator quality factor and coupling to the animal subject.

The resonant cavity can be excited by two or more orthogonal monopole feeds with a $\pi/2$ phase difference. The phase shift generates a circularly polarized (CP) mode such that the power transfer is invariant to the transverse orientation of the device. The resonant cavity and implantable devices described herein enable wireless powering of fully-implanted devices. This power transfer exhibits high uniformity across a surface and results in minimal radiative exposure for the experimenter. The described systems have considerable potential for investigating the neural basis for behaviors involving multiple interacting subjects.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A light delivery system, comprising:
   a resonant cavity chamber configured to generate electromagnetic energy, the resonant cavity chamber comprising a surface lattice of subwavelength apertures upon which an animal can be placed; and
   a wirelessly powered implantable device adapted to be implanted in the animal, the implantable device comprising:
   a circuit board;
   a power receiving coil coupled to the circuit board and adapted to receive electromagnetic energy from the resonant cavity;
   a rectifier coupled to the circuit board and the power receiving coil and adapted to convert the electromagnetic energy received in the power receiving coil into a DC current;

a micro-LED coupled to the circuit board and adapted to provide optogenetic stimulation to the animal.

2. The light delivery system of claim 1, wherein the implantable device is configured to be implanted on or adjacent to the animal's brain.

3. The light delivery system of claim 1, wherein the implantable device is configured to be implanted on or adjacent to the animal's spinal cord.

4. The light delivery system of claim 1, wherein the implantable device is configured to be implanted on or adjacent to nerve endings of one or more of the animal's limbs.

5. The light delivery system of claim 1, further comprising a conductive extension coupling the micro-LED to the circuit board.

6. The light delivery system of claim 1, wherein the implantable device has a volume ranging between 10 to 25 mm$^3$.

7. The light delivery system of claim 1, wherein the implantable device has a mass ranging from 20 to 50 mg.

8. The system of claim 1 further comprising a plurality of monopole feeds disposed in the resonant cavity chamber.

9. The system of claim 8, wherein the a plurality of orthogonal monopole feeds are arranged with 90 degrees phase differences so as to create circularly polarized waves.

* * * * *